(12) United States Patent
Miller et al.

(10) Patent No.: US 10,669,232 B2
(45) Date of Patent: Jun. 2, 2020

(54) PROCESSES AND SYSTEMS FOR RECOVERING METHANESULFONIC ACID IN PURIFIED FORM

(71) Applicant: Arkema Inc., King of Prussia, PA (US)

(72) Inventors: Jay F. Miller, Downingtown, PA (US); Gary S. Smith, Collegeville, PA (US); George C. Fortman, Conshohocken, PA (US); Vijay R. Srinivas, Exton, PA (US)

(73) Assignee: Arkema Inc., King of Prussia, PA (US)

( * ) Notice: Subject to any disclaimer, the term of this patent is extended or adjusted under 35 U.S.C. 154(b) by 0 days.

(21) Appl. No.: 16/485,464

(22) PCT Filed: May 8, 2018

(86) PCT No.: PCT/US2018/031466
§ 371 (c)(1),
(2) Date: Aug. 13, 2019

(87) PCT Pub. No.: WO2018/208701
PCT Pub. Date: Nov. 15, 2018

(65) Prior Publication Data
US 2020/0039926 A1 Feb. 6, 2020

Related U.S. Application Data

(60) Provisional application No. 62/504,577, filed on May 11, 2017.

(51) Int. Cl.
*C07C 303/44* (2006.01)
*C07C 309/04* (2006.01)

(52) U.S. Cl.
CPC .......... *C07C 303/44* (2013.01); *C07C 309/04* (2013.01)

(58) Field of Classification Search
CPC ... B01D 3/00; B01D 3/10; B01D 3/14; B01D 303/06; B01D 303/42; B01D 303/44;
(Continued)

(56) References Cited

U.S. PATENT DOCUMENTS 2,470,896 A * 5/1949 Mavity ................. C07C 303/06
562/96
6,531,629 B1 3/2003 Eiermann et al.
(Continued)

FOREIGN PATENT DOCUMENTS

WO WO 98/29385 7/1998
WO WO-9829385 A1 * 7/1998 ............. C07C 37/20

OTHER PUBLICATIONS

Elsevier Journal of Molecular Catalysis A: Chemical 211 (2004) 59-65 "Catalyzed Sulfonation of Methane to Methanesulfonic Acid"; Supid Mukhopadhyay & Alexis T. Bell.
(Continued)

*Primary Examiner* — Deborah D Carr
(74) *Attorney, Agent, or Firm* — Steven D. Boyd

(57) ABSTRACT

Aspects of the invention relate to systems and processes for recovering methanesulfonic acid, in a purified form, from a composition additionally including sulfur trioxide. In accordance with one aspect, the invention provides a process that includes separating a feed stream comprised of hydrocarbons, methanesulfonic acid, sulfur trioxide, and optionally sulfuric acid to produce a light stream comprised of hydrocarbons and a heavy stream comprised of methanesulfonic acid and sulfur trioxide; contacting (e.g., by mixing) the heavy stream with a reactive additive capable of reacting with sulfur trioxide, under conditions effective to cause reaction of the reactive additive with the sulfur trioxide to produce a heavy reaction product having a boiling point higher than the boiling point of methanesulfonic acid; and separating the heavy stream using a distillation column to
(Continued)

produce a distillate stream consisting essentially of methanesulfonic acid and a bottoms stream comprising the heavy reaction product.

20 Claims, 2 Drawing Sheets

(58) Field of Classification Search
CPC .. B01D 309/00; B01D 309/01; B01D 309/02; B01D 309/03; B01D 309/04
USPC .......................................................... 560/30
See application file for complete search history.

(56) References Cited

U.S. PATENT DOCUMENTS

2005/0070614 A1   3/2005  Richards
2016/0289181 A1*  10/2016 Ott ........................ C07C 409/44

OTHER PUBLICATIONS

The Reactions of Sulfur Trioxide, and use of its Adducts, with Organic Compounds; Everett E. Gilbert; Allied Chemical Corp., General Chemical Div., Nov. 6, 1961.

* cited by examiner

PROCESSES AND SYSTEMS FOR RECOVERING METHANESULFONIC ACID IN PURIFIED FORM

This present application is the national phase under 35 USC § 371 of prior PCT International Application Number PCT/US2018/031466 filed May 8, 2018 which designated the United States of America and claimed priority to U.S. Provisional Patent Application Ser. No. 62/504,577 filed May 11, 2017.

FIELD OF THE INVENTION

This disclosure relates to processes and systems for recovering methanesulfonic acid in purified form, and more particularly recovering anhydrous methanesulfonic acid from compositions additionally comprising sulfur trioxide.

BACKGROUND OF THE INVENTION

Traditional processes for recovering methanesulfonic acid from compositions comprising sulfur trioxide produces methanesulfonic acid having high concentrations of impurities. Additional processing steps to produce sufficiently pure methanesulfonic acid are typically inefficient and expensive. For example, previous methods for recovering methanesulfonic acid from compositions containing sulfur trioxide on an industrial scale require very high vacuums, which inevitably increase the cost of such processes, and produce recovered methanesulfonic acid having unacceptably high levels of sulfur trioxide.

Methanesulfonic acid compositions having above a trace amount of sulfur trioxide often are undesirable for many industrial processes. For example, methanesulfonic acid compositions having more than trace amounts of sulfur trioxide may produce undesirable by products or impurities with the addition of water.

In recent years, methanesulfonic acid has become more commoditized, which has driven down profit margins. Accordingly, there is a long standing need for improved systems and process for economically recovering anhydrous methanesulfonic acid in a highly purified form from compositions additionally comprising sulfur trioxide.

SUMMARY OF THE INVENTION

Aspects of the invention relate to systems and processes for recovering methanesulfonic acid, in a purified form, from a composition additionally including sulfur trioxide.

In accordance with one aspect, the invention provides a process that includes separating a feed stream comprised of hydrocarbons, methanesulfonic acid, sulfur trioxide, and optionally sulfuric acid to produce a light stream comprised of hydrocarbons and a heavy stream comprised of methanesulfonic acid and sulfur trioxide with optional sulfuric acid; contacting (e.g., by mixing) the heavy stream with a reactive additive capable of reacting with sulfur trioxide, under conditions effective to cause reaction of the reactive additive with the sulfur trioxide to produce a heavy reaction product having a boiling point higher than the boiling point of methanesulfonic acid; and separating the heavy stream using a distillation column to produce a distillate stream consisting essentially of methanesulfonic acid and a bottoms stream comprising the heavy reaction product.

Various aspects of the invention may be summarized as follows:

Aspect 1: A process for recovering anhydrous methanesulfonic acid, in a purified form, from a feed stream comprised of hydrocarbons, methanesulfonic acid, sulfur trioxide, and optionally sulfuric acid:

separating the feed stream to produce a light stream comprised of hydrocarbons and a heavy stream comprised of methanesulfonic acid and sulfur trioxide with the optional sulfuric acid;

contacting the heavy stream with a reactive additive capable of reacting with sulfur trioxide (e.g., water), under conditions effective to cause reaction of the reactive additive with the sulfur trioxide to produce a heavy reaction product (e.g., sulfuric acid) having a boiling point higher than the boiling point of sulfur trioxide; and separating the heavy stream using a distillation column to produce a distillate stream consisting essentially of methanesulfonic acid and a bottoms stream comprising the heavy reaction product.

Aspect 2. The process of Aspect 1, wherein separating the heavy stream further comprises recovering a stream consisting essentially of hydrocarbons using a vapor-liquid separator.

Aspect 3. The process of Aspects 1-2, wherein the step of contacting the heavy stream with the reactive additive comprises mixing the reactive additive and the heavy stream using at least one of a mixer drum or a static mixer.

Aspect 4. The process of Aspects 1-3, further comprising a step of reacting sulfur trioxide with methane using a reactor to produce the feed stream comprising hydrocarbons, methanesulfonic acid, sulfur trioxide, and optionally sulfuric acid.

Aspect 5. The process of Aspect 4, wherein a peroxide initiator is fed to the reactor.

Aspect 6. The process of Aspect 5, wherein the peroxide initiator is one or more compounds selected from the group consisting of $H_2O_2$, and reaction products of $H_2O_2$ with $SO_3$, organosulfonic acids, phosphoric acids, phosphonic acids, or carboxylic acids.

Aspect 7. The process of Aspect 5, wherein the peroxide initiator is one or more compounds selected from the group consisting of peroxymonosulfuric acid, peroxydisulfuric acid, methanesulfonylperoxysulfuric acid, dimethanesulfonyl peroxide, and organic salts, inorganic salts, or esters thereof.

Aspect 8. The process of Aspects 1-7, wherein the feed stream further comprises sulfuric acid.

Aspect 9. The process of Aspects 1-8, wherein the reactive additive is water.

Aspect 10. The process of Aspects 1-8, wherein the reactive additive is at least one compound selected from the group consisting of alcohols, ethers, alkyl benzenes, and alpha olefins.

Aspect 11. The process of Aspects 1-8, wherein the distillation column is operated at a pressure of 0.22 mbar to 50 mbar.

Aspect 12. The process of claim Aspect 11, wherein the distillation column is operated at a pressure of 4 mbar to 30 mbar.

Aspect 13. The process of Aspect 12, wherein the distillation column is operated at a pressure of 6 mbar to 14 mbar.

Aspect 14. The process of Aspect 13, wherein the distillation column is operated at a pressure of 8 mbar to 12 mbar.

Aspect 15. The process of Aspects 1-14, wherein the distillate stream comprises not more than 500 ppm of sulfuric acid or an equivalent thereof.

Aspect 16. The process of Aspect 15, wherein the distillate stream comprises not more than 400 ppm of sulfuric acid or an equivalent thereof.

Aspect 17. The process of Aspect 16, wherein the distillate stream comprises not more than 300 ppm of sulfuric acid or an equivalent thereof.

Aspect 18. The process of Aspect 17, wherein the distillate stream comprises not more than 150 ppm of sulfuric acid or an equivalent thereof.

Aspect 19. The process of Aspect 1, wherein the distillate stream consists of methanesulfonic acid and not more than 50 ppm of impurities (compounds other than methanesulfonic acid or its methyl ester, e.g., hydrocarbons, sulfur trioxide, and/or sulfuric acid).

Aspect 20. The process of claim 1, wherein the distillate stream comprises essentially no sulfur trioxide.

Aspect 21. The process of Aspect 1-19, wherein the distillate stream comprises not more than 60 ppm of sulfur trioxide.

Aspect 22. The process of Aspect 21, wherein the distillate stream comprises not more than 40 ppm of sulfur trioxide.

BRIEF DESCRIPTION OF THE DRAWINGS

The invention is best understood from the following detailed description when read in connection with the accompanying drawings, with like elements having the same reference numerals. According to common practice, various features of the drawings are not drawn to scale unless otherwise indicated. On the contrary, the dimensions of the various features may be expanded or reduced for clarity. Included in the drawings are the following figures.

DETAILED DESCRIPTION OF THE INVENTION

Figure 1:
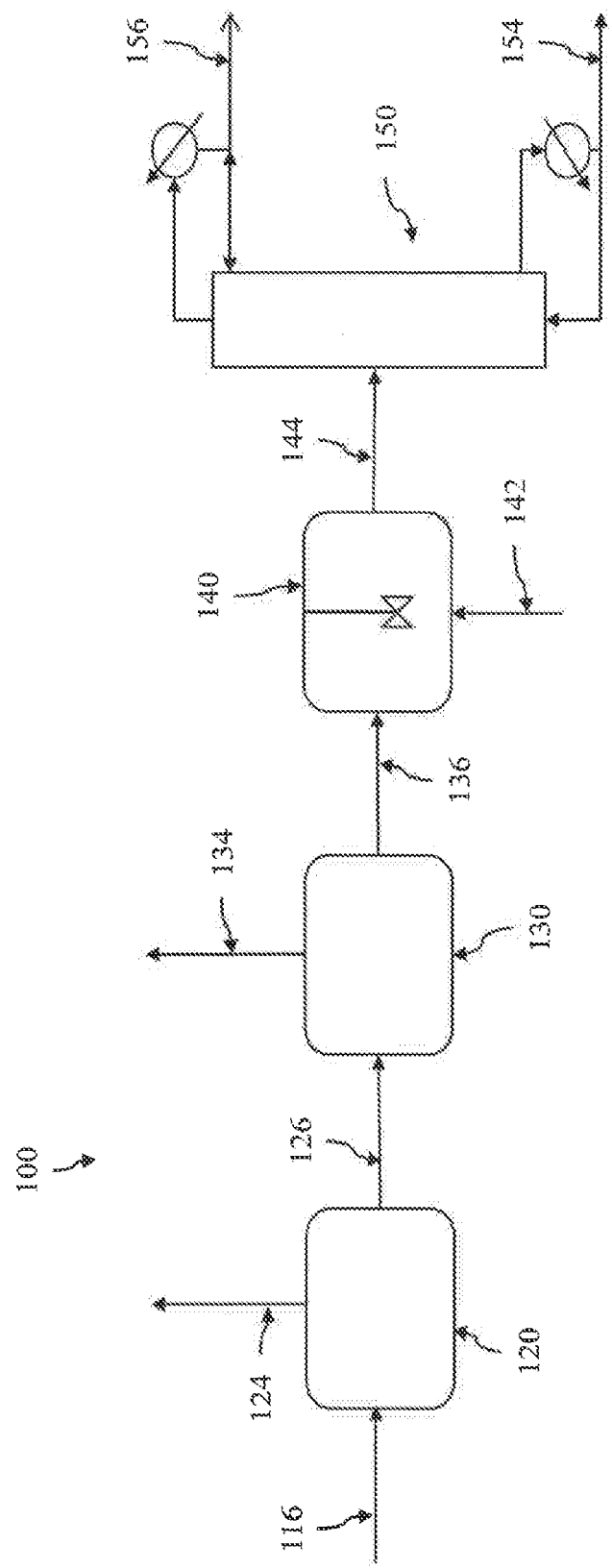
FIG. 1 is a schematic of a separation system for recovering methanesulfonic acid in purified form from compositions including sulfur trioxide in accordance with aspects of the invention.

Aspects of the invention are directed to processes and systems for recovering methanesulfonic acid in purified form, and more particularly recovering anhydrous methanesulfonic acid from compositions additionally comprising sulfuric compounds, such as sulfur trioxide.

The present inventors have discovered that embodiments of the present invention enable the economic recovery of methanesulfonic acid, in a purified form, from compositions that include sulfuric compounds, such as sulfur trioxide and sulfuric acid. Moreover, using embodiments of the invention, it is possible to produce a methanesulfonic acid product containing insignificant amounts of sulfur trioxide, thereby producing a composition of methanesulfonic acid having improved stability and industrial usability. In one embodiment, the recovered methanesulfonic acid has 500 ppm of sulfur trioxide or less, e.g., 180 ppm sulfur trioxide or less, preferably 120 ppm sulfur trioxide or less, preferably 60 ppm sulfur trioxide or less and/or preferably 40 ppm sulfur trioxide or less. In another embodiment, the recovered methanesulfonic acid has 500 ppm or less, preferably 400 ppm or less, preferably 300 ppm or less, preferably 150 ppm or less, and/or preferably 50 ppm or less of sulfuric acid or equivalents thereof (e.g., compounds capable of reactions to form sulfuric acid, such as sulfur trioxide, and compounds obtained from or which are derivatives of sulfuric acid, such as ethyl hydrogen sulfate).

As used herein, the term "sulfuric compound" means any compound containing sulfur other than methanesulfonic acid.

FIG. 1 illustrates a separation system 100 for recovering anhydrous methanesulfonic acid in purified form from compositions additionally comprising sulfuric compounds such as sulfur trioxide. As a general overview, separation system 100 includes one or more vapor-liquid separators (e.g., first vapor-liquid separator 120 and second vapor-liquid separator 130), mixer 140, and distillation column 150.

First vapor-liquid separator 120 is adapted for separating a feed stream 116 that comprises hydrocarbons (which may be a single hydrocarbon, e.g., methane), methanesulfonic acid, sulfur trioxide, and optionally sulfuric acid to produce light stream 124 comprising hydrocarbons, e.g., methane, and heavy stream 126 comprising methanesulfonic acid and sulfur trioxide. Feed stream 116 may include methanesulfonic acid, sulfuric acid, methane, sulfur trioxide and optionally sulfuric acid. Light stream 124 may have a composition of 70% or more hydrocarbons by weight, e.g., 80% or more hydrocarbons by weight, 90% or more hydrocarbons by weight, 95% or more hydrocarbons by weight and/or 97.5% or more hydrocarbons by weight.

First vapor-liquid separator 120 is operated at a temperature and pressure suitable for producing light stream 124 and heavy stream 126. For example, first vapor-liquid separator 120 may be operated at a pressure of 60 psi to 140 psi. In one embodiment, first vapor-liquid separator 120 is operated at 80 psi to 120 psi. In another embodiment, first vapor-liquid separator 120 is operated at about 100 psi. First vapor-liquid separator 120 may be configured as a flash drum.

As a result of employing first vapor-liquid separator 120, heavy stream 126 has a composition having a reduced amount of hydrocarbons. For example, first vapor-liquid separator 120 may remove a majority of the hydrocarbons from feed stream 116, such that heavy stream 126 includes, e.g., 500 ppm of hydrocarbons or less, preferably 200 ppm of hydrocarbons or less, preferably 100 ppm of hydrocarbons or less, preferably 20 ppm of hydrocarbons or less, preferably 10 ppm of hydrocarbons or less, etc. In one embodiment, heavy stream 126 is essentially free of hydrocarbons. The hydrocarbons of heavy stream 126 and/or feed stream 126 may comprise or consist essentially of methane. Although heavy stream 126 is further separated using second vapor-liquid separator 130 in FIG. 1, other embodiments of the present invention may separate heavy stream 126 using other processing units or may mix heavy stream 126 with a reactive additive (e.g., as discussed below) prior to further separation processes.

Second vapor-liquid separator 130 may be adapted for recovering light stream 134 consisting essentially of hydrocarbons and producing heavy stream 136. Second vapor-liquid separator 130 may be configured as a flash drum. Preferably, second vapor-liquid separator 130 removes a majority of the hydrocarbons from heavy stream 126, such that heavy stream 136 includes, e.g., 50 ppm of hydrocarbons or less, preferably 30 ppm of hydrocarbons or less, preferably 10 ppm of hydrocarbons or less, preferably 5 ppm of hydrocarbons or less, preferably 2 ppm of hydrocarbons or less. In one embodiment, heavy stream 136 is essentially free of hydrocarbons. As mentioned above, the hydrocarbons may comprise or consist essentially of methane.

Heavy stream 136 is mixed with a reactive additive adapted for reacting with the sulfur trioxide of heavy stream 136. The reactive additive may be any compound that reacts with $SO_3$ provided that the reactive additive and its reaction products can be separated from methanesulfonic acid. Suitable reactive additives include, but are not limited to: water, alcohols, ammonia, amines (e.g., primary or secondary amines), olefins, aromatics, ketones, or compounds with a NH functional group, OH functional group, or halogen functional group and the like. Such reactive species are discussed, for example, in Everett E. Gilbert, "The Reactions of Sulfur Trioxide, and Its Adducts, with Organic Compounds, Chem. Rev., 1962, 62 (6), pp. 549-589 (incorporated herein by reference in its entirety for all purposes).

The reactive additive is selected to be capable of reacting with sulfur trioxide to form a heavy reaction product having a boiling point higher than that of methanesulfonic acid. For example, water may be used as the reactive additive, leading to the production of sulfuric acid as the heavy reaction product. Conversion of the sulfur trioxide to a heavy reaction product facilitates the purification of the methanesulfonic acid since, as previously mentioned, it is difficult to completely remove sulfur trioxide from methanesulfonic acid using distillation methods or to achieve the low levels of impurities mentioned herein (e.g., less than 500, 400, 300, 180, 150, 120, 60, or 50 ppm). In advantageous embodiments of the invention, the reactive additive is selected such that it results in the production of a heavy reaction product from sulfur trioxide which has a boiling point (at 10 mm Hg) at least 10° C., at least 20° C., at least 35° C., at least 50° C., at least 65° C. or at least 80° C. higher than the boiling point of methanesulfonic acid (167° C. at 10 mm Hg).

In one embodiment, the reactive additive consists essentially of water. In another embodiment, the reactive additive consists of $H_2O$ and trace impurities. The reactive additive may be mixed into heavy stream 136 at an excess with respect to the sulfur trioxide to be reacted. For example, the reactive additive may be may be mixed into heavy stream 136 at an excess of, e.g., 10% or more on a molar basis, preferably 20% or more on a molar basis, preferably 30% or more on a molar basis, preferably 35% or more on a molar basis, preferably 40% or more on a molar basis, preferably 45% or more on a molar basis, preferably 50% or more on a molar basis, preferably 55% or more on a molar basis, etc., with respect to the sulfur trioxide to be reacted.

Mixer 140 may be, e.g., a mixing drum, a static mixer, or the like, that is configured to mix heavy stream 136 and the reactive additive, which may be introduced by input stream 142, by way of batch or continuous operation to produce mixed stream 144. Mixer 140 may include a cooling jacket, heat exchanger, or the like to reduce the temperature of mixed stream 144 leaving mixer 140 as the reaction between the reactive additive and the sulfur trioxide may be exothermic. In one embodiment, a cooling jacket or heat exchanger is not used as the addition of water, and the exothermic reaction resulting therefrom, advantageously preheats the mixture as preparation for the next step. For example, using water as the reactive additive may produce a highly exothermic reaction with sulfur trioxide that may or may not require a cooling jacket. Although mixing of heavy stream 136 with a reactive additive occurs by mixer 140 in system 100 as illustrated in FIG. 1, system 100 may be modified such that heavy stream 136 and the reactive additive mix within one or more pipes or process units. For example, system 100 may be configured to produce turbulent flow properties for heavy stream 126, which mix the reactive additive with heavy stream 136.

As illustrated in FIG. 1, mixed stream 144 is separated using distillation column 150. Although system 100 as illustrated in FIG. 1 utilizes distillation column 150 to separate mixed stream 144, system 100 may be modified to use a distillation column 150 and one or more vapor-liquid separators to separate mixed stream 144.

Distillation column 150 may be configured to optimize the amount of methanesulfonic acid recovered in distillate stream 156 or configured to optimize the purity of methanesulfonic acid recovered in distillate stream 156. Distillation column 150 may be configured as a packed bed column or configured to have a plurality of trays or the like. Preferably, the column will contain structured packing due to the potential thermal instability of methanesulfonic acid. In one embodiment, distillation column 150 is configured as a packed bed having an equivalence of thirty ideal trays. The packed bed may be formed of structured packing, e.g., Koch-Glitsch, Flexipack™ 1Y. Distillation column 150 may be operated at a pressure of 0.22 mbar to 20 mbar, preferably 4 mbar to 16 mbar, and/or preferably 8 mbar to 12 mbar. In one embodiment, distillation column 150 is operated at a pressure of about 10 mbar.

Figure 2:
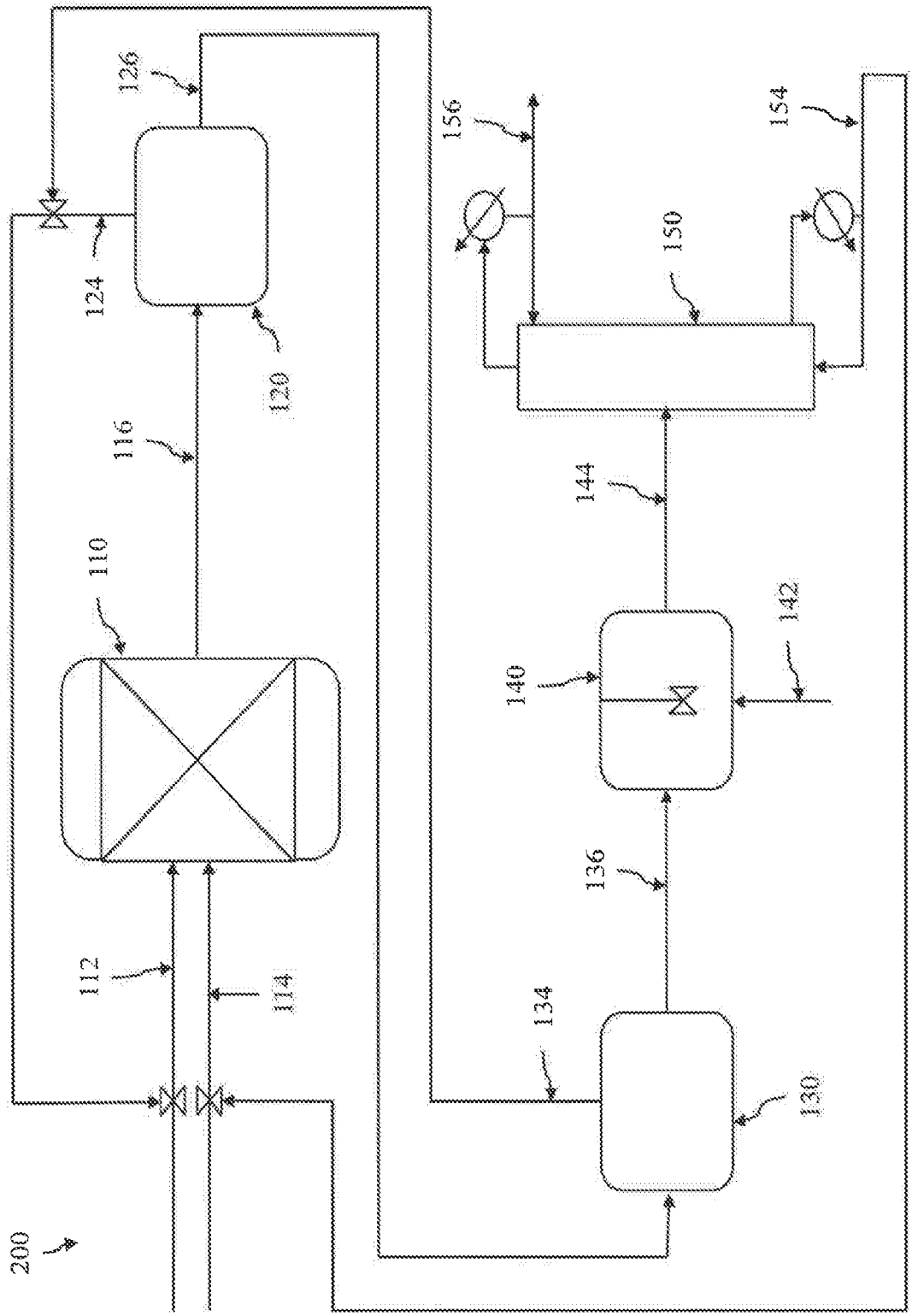
FIG. 2 is a schematic of a manufacturing system employing a reactor for producing methanesulfonic acid and the separation system of FIG. 1 according to aspects of the invention.

Distillation column 150 is configured to produce distillate stream 156 consisting essentially of methanesulfonic acid and a bottoms 154 stream comprising sulfuric compounds. Bottoms stream 154 may have a composition including sulfuric compounds, methanesulfonic acid, and impurities (e.g., compounds or substances other than sulfuric compounds and methanesulfonic acid). For example, if separation system 100 is operating under methanesulfonic acid rich conditions, bottoms stream 154 may contain 50-90% methanesulfonic acid with the remainder being sulfuric compounds and impurities. Alternatively, separation system 100 may be operated under conditions rich in sulfuric-compounds, such that bottoms stream 154 contains sulfuric compounds and, e.g., 50% or less of methanesulfonic acid by weight, preferably 35% or less of methanesulfonic acid by weight, preferably 5% or less of methanesulfonic acid by weight. In one embodiment, bottoms stream 154 consists essentially of sulfuric compounds. In another embodiment, bottoms stream 154 consists of sulfuric compounds and trace compounds. Operating distillation column 150 under methanesulfonic acid rich conditions may reduce the costs associated with constructing and/or operating distillation column 150. Operating distillation column 150 under sulfuric rich conditions may enable a higher percentage of the methanesulfonic acid in mixed stream 144 to be recovered in distillate stream 156. Under certain operation conditions, methanesulfonic acid rich refers to a mixed stream 144 (e.g., as seen in FIG. 2) having 50% or more methanesulfonic acid, while sulfuric rich refers to a mixed stream 144 having 50% or more sulfuric compounds. However, methanesulfonic acid rich and sulfuric rich conditions vary depending on the operating conditions of distillation column 150. Another consideration is that the distillate rate should match the production rate of reactor 110.

Distillate stream 156 may have a composition that is substantially pure methanesulfonic acid, e.g., a composition of 90% or more methanesulfonic acid by weight, more preferably 95% or more methanesulfonic acid by weight, more preferably 96.5% or more methanesulfonic acid by weight, more preferably 98% or more methanesulfonic acid by weight, more preferably 99% or more methanesulfonic acid by weight, more preferably 99.5% or more methanesulfonic acid by weight, and/or more preferably 99.8% or more methanesulfonic acid by weight. In one embodiment, distillate stream 156 has an essentially pure composition of methanesulfonic acid. In another embodiment, distillate stream 156 has a composition consisting of methanesulfonic acid and trace impurities. Preferably, distillate stream 156 has 500 ppm of sulfuric compounds or less, more preferably 400 ppm of sulfuric compounds or less, more preferably 300 ppm of sulfuric compounds or less, more preferably 150 ppm of sulfuric compounds or less, more preferably 50 ppm of sulfuric compounds or less. For example, the recovered methanesulfonic acid may have effectively zero sulfur trioxides. In one embodiment, the recovered methanesulfonic acid has 1 ppm sulfur trioxide or less, e.g., 0.1 ppm sulfur trioxide or less, preferably 0.01 ppm sulfur trioxide or less, and/or preferably 0.001 ppm sulfur trioxide or less. Additionally and/or alternatively, distillate stream 156 may have less than or equal to 500 ppm of sulfuric acid or equivalents thereof (e.g., products of sulfuric acid including vapors, such as sulfur trioxide, and liquids, such as ethyl hydrogen sulfate). For example, the recovered methanesulfonic acid may have less than or equal to 400 ppm of sulfuric acid or equivalents thereof, preferably less than or equal to 300 ppm of sulfuric acid or equivalents thereof, preferably less than or equal to 150 ppm of sulfuric acid or equivalents thereof, preferably less than or equal to 60 ppm of sulfuric acid or equivalents thereof, or preferably less than or equal to 50 ppm of sulfuric acid or equivalents thereof.

By employing system 100, distillation column 150 advantageously may be operated at pressures that are more efficient and economical than distillation columns operated under higher vacuums. In addition to the ability to operate distillation column 150 at more desirable pressures, system 100 produces methanesulfonic acid having a sufficiently low amount of impurities—namely sulfuric compounds, such as sulfur trioxide. By using system 100, and methods disclosed herein, highly pure methanesulfonic acid, which may exceed the most stringent commercial purity standards, may be produced at commercially advantageous costs.

FIG. 2 illustrates a manufacturing system 200 for producing and recovering methanesulfonic acid according to aspects of the invention. As a general overview, manufacturing system 200 includes reactor 110, first vapor-liquid separator 120, second vapor-liquid separator 130, mixer 140, and distillation column 150. Manufacturing system 200 is illustrated as employing separation system 100. Accordingly, where manufacturing system 200 utilizes features/system equipment of separation system 100, the same reference numbers are applied as those in FIG. 1.

Reactor 110 is configured to produce methanesulfonic acid from sulfur trioxide and methane. For example, reactor 110 may receive reactor feed stream 112, having a composition of methane, and reactor feed stream 114, having a composition of sulfur trioxide, sulfuric acid, and optionally containing MSA. In one embodiment, one or more peroxide initiators is added to reactor 110 to catalyze the desired reactions. Suitable peroxide initiators include, but are not limited to, $H_2O_2$, and reaction products of $H_2O_2$ with $SO_3$, organosulfonic acids, phosphoric acids, phosphonic acids, or carboxylic acids. The reaction products may be in the presence of methanesulfonic acid. Peroxide initiators selected from the group consisting of peroxymonosulfuric acid (HOO—$SO_3H$), peroxydisulfuric acid (HOSO$_2$—OO—$SO_2OH$), methanesulfonylperoxysulfuric acid ($CH_3SO_2$—OO—$SO_2OH$), dimethanesulfonyl peroxide ($CH_3SO_2$—OO—$SO_2CH_3$), and organic salts, inorganic salts, or esters thereof, may be advantageous under certain processing conditions. Reactor 110 is configured to produce feed stream 116 having a composition comprising hydrocarbons, methanesulfonic acid, sulfur trioxide, and optionally sulfuric acid.

Although reactor 110 is configured to produce methanesulfonic acid from sulfur trioxide and methane in FIG. 2, reactor 110 may be configured to produce methanesulfonic acid by way of other reaction mechanisms and/or using other reactants.

Manufacturing system 200 may be configured to recycle compounds recovered from separation system 100 to reactor feed stream 112 and/or reactor feed stream 114. For example, light stream 124 having a composition comprising of hydrocarbons may be recycled into reactor 110 by way of reactor feed stream 112. Additionally and/or alternatively, light stream 124 and/or 134 may be used as fuel, e.g., for one or more of the process units of system 200. Bottoms stream 154 of distillation column 150, which has a composition comprising sulfuric compounds (e.g., sulfuric acid) and optionally methanesulfonic acid, may be recycled to reactor 110 by way of reactor feed stream 114.

EXAMPLES

The following examples are non-limiting embodiments of the present invention, included herein to demonstrate the advantageous utility obtained from aspects of the present invention.

Example 1

A reaction stream of 4,950 pph sulfur trioxide ("$SO_3$") is mixed with 11,550 pph sulfuric acid ("$H_2SO_4$") and enters a reactor, where 2,310 pph methane ("$CH_4$") is added at a pressure of 40 bara. A reaction initiator of, e.g., a 50% hydrogen peroxide solution, flows at about 75 pph into the reactor. The mixture flows through the reactor, or systems of reactors, obtaining a 95% conversion of $SO_3$ to methanesulfonic acid ("MSA"). Obtaining greater than 95% conversion can be done, with the costs being extremely high to achieve >99.9% conversion. Even with 99.9% $SO_3$ conversion there will remain over 300 ppm $SO_3$ in the reaction product.

The reactor outlet stream is sent to an isentropic flash at 100 psi. Most of the methane is removed and either recovered or burned for fuel value. Only about 10% of the remaining $SO_3$ goes overhead with the methane. The resulting stream contains about 5455 pph MSA, 11,750 pph sulfuric acid, 37 pph methane and about 210 pph $SO_3$.

The heavy stream from the flash has water added in excess of the amount of $SO_3$ to ensure all the $SO_3$ is converted to sulfuric acid. This can be done by analysis or by mass balance. For this example there is 1.35 times the molar amount of water calculated to be necessary to ensure all the $SO_3$ converts. This reactor is isentropic, but due to the small amount of water, even though the reaction between $SO_3$ and water is highly exothermic, the tails stream is only heated by about 4° C.

The heavy stream is sent to a low pressure isentropic flash, at about 20 mm Hg, to remove just about all the methane.

The heavy stream from the second flash is sent to a distillation column with 30 ideal stages, with structured packing, e.g., Koch-Glitsch Flexipac 1Y. The column head pressure is about 10 mm Hg and the condenser is operated such that 5% goes out as vapor and 95% gets condensed. The reflux ratio is set at 5 (wgt basis). The final concentration of $H_2SO_4$ in the MSA is about 35 ppm. There is no $SO_3$ in the MSA. So, if and when water is added to the anhydrous MSA to make a 70% MSA solution, the sulfuric acid concentration will be <35 ppm on an anhydrous basis.

Example 2

This Example shows a system employing a very high conversion of $SO_3$ in the reactor section. The feed is the same as discussed in Example 1. The only major change is a polishing reactor is employed after a first set of reactors to achieve a $SO_3$ conversion of 99%.

The outlet stream of the reactor section contains about 5684 pph MSA, 11,754 pph $H_2SO_4$, 1361 pph methane and 48 pph $SO_3$.

After a first flash there is still 42 pph $SO_3$ in the MSA/$H_2SO_4$. If the MSA was separated from the $H_2SO_4$, a large portion of the $SO_3$ would remain in the MSA stream. The concentration of $SO_3$ remaining in the MSA stream would be about 7333 ppm.

However, in this Example, water is added to convert the $SO_3$ to $H_2SO_4$. The stream is then vacuum flashed and sent to the same distillation column. The resulting MSA contains no $SO_3$ and 33 ppm $H_2SO_4$.

Comparative Example 1

This Comparative Example demonstrates the benefits of the invention by illustrating the problems arising from separation processes outside the scope of the invention.

The feeds of this Comparative Example are the same as the feeds used in Example 2. The only difference is that no water is added to convert the $SO_3$ to $H_2SO_4$. In this case, the MSA has an $SO_3$ impurity level of about 40 ppm, in addition to about 33 ppm $H_2SO_4$. When the anhydrous MSA is mixed with water, the $SO_3$ will be converted to $H_2SO_4$ and the MSA will have over 80 ppm $H_2SO_4$ in it. This amount of sulfuric acid renders the MSA undesirable for many industrial applications.

Within this specification, embodiments have been described in a way which enables a clear and concise specification to be written, but it is intended and will be appreciated that embodiments may be variously combined or separated without departing from the invention. For example, it will be appreciated that all preferred features described herein are applicable to all aspects of the invention described herein.

In some embodiments, the invention herein can be construed as excluding any element or process step that does not materially affect the basic and novel characteristics of the process. Additionally, in some embodiments, the invention can be construed as excluding any element or process step not specified herein.

Although the invention is illustrated and described herein with reference to specific embodiments, the invention is not intended to be limited to the details shown. Rather, various modifications may be made in the details within the scope and range of equivalents of the claims and without departing from the invention.

The invention claimed is:

1. A process for recovering anhydrous methanesulfonic acid, in a purified form, from a feed stream comprised of hydrocarbon, methanesulfonic acid and sulfur trioxide comprising:

separating the feed stream to produce a light stream comprised of hydrocarbons and a heavy stream comprised of methanesulfonic acid and sulfur trioxide;
contacting the heavy stream with a reactive additive capable of reacting with sulfur trioxide under conditions effective to cause reaction of the reactive additive with the sulfur trioxide to produce a heavy reaction product having a boiling point higher than the boiling point of sulfur trioxide; and
separating the heavy stream using a distillation column to produce a distillate stream consisting essentially of methanesulfonic acid and a bottoms stream comprising the heavy reaction product.

2. The process of claim 1, wherein separating the heavy stream further comprises recovering a stream consisting essentially of hydrocarbons using a vapor-liquid separator.

3. The process of claim 1, wherein the step of contacting the heavy stream with the reactive additive further comprises mixing the reactive additive and the heavy stream using at least one mixer.

4. The process of claim 1, further comprising reacting sulfur trioxide with methane using a reactor to produce the feed stream comprising hydrocarbons, methanesulfonic acid, sulfur trioxide, and optionally sulfuric acid.

5. The process of claim 4, wherein a peroxide initiator is fed to the reactor.

6. The process of claim 1, wherein the feed stream further comprises sulfuric acid.

7. The process of claim 1, wherein the reactive additive is water.

8. The process of claim 1, wherein the reactive additive is at least one compound selected from the group consisting of alcohols, ethers, alkyl benzenes, and alpha olefins.

9. The process of claim 1, wherein the distillation column is operated at a pressure of 0,22 mbar to 50 mbar.

10. The process of claim 9, wherein the distillation column is operated at a pressure of 4 mbar to 30 mbar.

11. The process of claim 10, wherein the distillation column is operated at a pressure of 6 mbar to 14 mbar.

12. The process of claim 11, wherein the distillation column is operated at a pressure of 8 mbar to 12 mbar.

13. The process of claim 1, wherein the distillate stream comprises not more than 500 ppm of sulfuric acid or an equivalent thereof.

14. The process of claim 13, wherein the distillate stream comprises not more than 400 ppm of sulfuric acid or an equivalent thereof.

15. The process of claim 14, wherein the distillate stream comprises not more than 300 ppm of sulfuric acid or an equivalent thereof.

16. The process of claim 15, wherein the distillate stream comprises not more than 150 ppm of sulfuric acid or an equivalent thereof.

17. The process of claim 1, wherein the distillate stream consists of methanesulfonic acid and less than 50 ppm of impurities.

18. The process of claim 1, wherein the distillate stream comprises essentially no sulfur trioxide.

19. The process of claim 1, wherein the distillate stream comprises 60 ppm of sulfur trioxide or less.

20. The process of claim 19, wherein the distillate stream comprises 40 ppm of sulfur trioxide or less.

* * * * *